United States Patent [19]

Anderson

[11] 4,108,906
[45] Aug. 22, 1978

[54] HALOGENATED ARYL COMPOUNDS AND PROCESSES FOR PREPARING THE SAME

[75] Inventor: Arnold L. Anderson, Alma, Mich.

[73] Assignee: Velsicol Chemical Corporation, Chicago, Ill.

[21] Appl. No.: 330,838

[22] Filed: Feb. 8, 1973

Related U.S. Application Data

[63] Continuation-in-part of Ser. No. 260,240, Jun. 6, 1972, abandoned.

[51] Int. Cl.² .......................................... C07C 149/00
[52] U.S. Cl. ........................... 260/609 R; 260/45.9 R; 260/465 F; 260/465 G; 260/570.5 P; 260/570.5 S; 260/570.7; 260/570.9; 260/590 D
[58] Field of Search ............ 260/570.7, 625 R, 609 R, 260/609 F

[56] References Cited

U.S. PATENT DOCUMENTS

| | | | |
|---|---|---|---|
| 2,738,351 | 3/1956 | Dickinson et al. | 260/293.4 |
| 2,930,815 | 3/1960 | Nedwick et al. | 260/609 X |
| 3,787,506 | 1/1974 | Ungefug et al. | 260/613 |

OTHER PUBLICATIONS

Brookes et al., "Chemical Abstracts", vol. 52, pp. 4543-4544 (1958).
Koenigs et al., "Chemical Abstracts", vol. 26, p. 706 (1932).

*Primary Examiner*—Robert V. Hines
*Attorney, Agent, or Firm*—Robert M. Phipps

[57] ABSTRACT

Halogenated aryl compounds having the formula

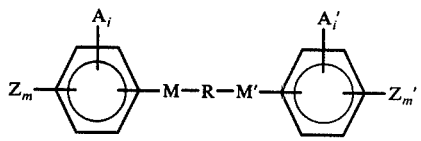

wherein Z is bromine or chlorine, m and m' are integers having a value of 1-5, i and i' are integers having a value of 0-2, R is herein defined, M and M' are each independent and are from the group oxygen, nitrogen or sulfur with the proviso that M and M' cannot concurrently be oxygen in both cases, and A is chlorine, cyano, nitro, lower alkoxy, lower alkyl, fluorine, dialkylamino, phenyl, halo-phenyl, benzyl, or halo-benzyl, and which compounds are found useful as flame retardants for various polymeric systems.

2 Claims, No Drawings

HALOGENATED ARYL COMPOUNDS AND PROCESSES FOR PREPARING THE SAME

This application is a continuation-in-part of copending application Ser. No. 260,240, filed June 6, 1972 and now abandoned. The entire specification of this case, Ser. No. 260,240, is to be considered as incorporated herein by reference.

The prior art considered in conjunction with the preparation of this application is as follows: U.S. Pat. Nos. 2,130,990; 2,186,367; 2,329,033; 3,666,692; 3,686,320; 3,658,634, German Patent No. 1,139,636; German Patent No. 2,054,522; Japanese Patent No. (72) 14,500 as cited in Volume 77, Chemical Abstracts, column 153737k (1972); Chemical Abstracts, Volume 13, column 448[5]; Chemical Abstracts, Volume 31, column 7045[9]; and Journal of the Chemical Society, pages 2972–2976 (1963). All of these publications are to be considered as incorporated herein by reference.

The present invention relates to a new class of aromatic compounds and processes for preparing such compounds. More particularly, the present invention has as its primary object providing halogenated aryl compounds and processes for preparing the same.

According to the present invention, there is provided a new and useful class of halogenated aryl compounds corresponding to the following formula:

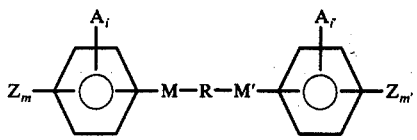
(I)

In Formula I above, Z is bromine or chlorine, m and m' are integers each independently having a value of 1–5; i and i' are integers each independently having a value of 0–2; M and M' are each independent and are from the group oxygen, nitrogen, sulfur with the proviso that M and M' cannot concurrently be oxygen in both cases; A is from the group chlorine, cyano (—CN), nitro (—$NO_2$), lower alkoxy (e.g. —$OCH_3$, $OC_2H_5$) lower alkyl (e.g. $CH_3$, $C_2H_5$, $C_3H_4$, $C_4H_9$), fluorine, dialkylamino e.g. —$N(CH_3)_2$, $N(C_2H_5)_2$, phenyl (-$C_6H_5$), halo-phenyl, benzyl (—$CH_2C_6H_5$), and halo-benzyl; and R is from the group (a) alkylene: branched or straight or halo-branched chain group having from one to six carbon atoms (e.g. $CH_2$, $C_2H_4$, $C_3H_6$, $C_4H_8$, —$C(CH_3)H$—, —$(CH_3)C(CH_3)$—, —$C(CH_2Cl)H$—, —$C(CHBr_2)H$—.
(b) $CH_2$—$CH(OH)$—$CH_2$
(c) $CH_2$—$CH(CH_2HO)$—$CH_2$
(d) $(CH_2)_w$—O—$(CH_2)_w$ where w = 1–6
(e)

$CH_2$—⬡$X_n$—$CH_2$ where X = H, Cl, Br; n = 4

(f) $CH_2$—$C(O)$—$CH_2$
(g) $CH_2$—CH with phenyl ring
(h) $H_2C$—⬡S—$CH_2$ where S = saturated ring In Formula I, $i + m$ or $i' + m'$ is not greater than 5.

It is to be understood that all of the compounds falling within the above Formula I and as heretofore defined are generically described herein as "halogenated aryl" compounds.

The halogenated aryl compounds are found to be compatible with and effective additives for various polymeric systems to make the resultant polymer flame retardant.

Illustrative (but without limitation) of some of the present invention halogenated aryl compounds are shown below:

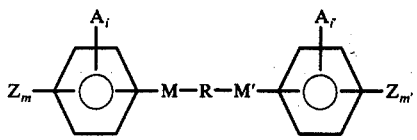
(I)

the exemplary definitions of A, Z, M, M', R, m, m', i and i' are listed in Table I.

Table I

| Compound No. | Z | m | m' | A | i | i' | R | M | M' |
|---|---|---|---|---|---|---|---|---|---|
| 1 | Br | 1 | 1 | — | 0 | 0 | $C_2H_4$ | S | S |
| 2 | Br | 1 | 3 | — | 0 | 0 | $C_2H_4$ | S | O |
| 3 | Br | 2 | 2 | Cl | 1 | 1 | $C_3H_6$ | O | N |
| 4 | Br | 2 | 2 | —CN | 1 | 1 | $C_2H_4$ | N | N |
| 5 | Br | 2 | 2 | —$NO_2$ | 1 | 1 | $C_2H_4$ | O | N |
| 6 | Cl | 2 | 2 | —$OCH_3$ | 1 | 1 | $C_2H_4$ | S | S |
| 7 | Br | 3 | 3 | —$OCH_3$ | 1 | 1 | $C_2H_4$ | S | O |
| 8 | Br | 2 | 2 | —$CH_3$ | 1 | 1 | $C_2H_4$ | N | N |
| 9 | Br | 2 | 2 | F | 1 | 1 | $C_3H_6$ | S | S |
| 10 | Br | 2 | 2 | —$N(CH_3)_2$ | 1 | 1 | $C_2H_4$ | N | N |
| 11 | Br | 2 | 2 | —$C_6H_5$ | 1 | 1 | $C_2H_4$ | N | S |
| 12 | Cl | 2 | 2 | —$C_6H_3Br_2$ | 1 | 1 | $C_2H_4$ | N | S |
| 13 | Br | 2 | 2 | —$CH_2C_6H_5$ | 1 | 1 | $C_2H_4$ | S | S |
| 14 | Br | 2 | 2 | —$CH_2C_6H_3Br_2$ | 1 | 1 | $C_2H_4$ | N | N |
| 15 | Cl | 3 | 3 | —$C_6H_3Cl_2$ | 1 | 1 | $C_3H_6$ | N | N |
| 16 | Br | 3 | 3 | F | 1 | 1 | $C_6H_{12}$ | N | O |
| 17 | Br | 2 | 1 | —$N(CH_3)_2$ | 1 | 0 | $C_3H_6$ | N | S |
| 18 | Br | 2 | 3 | —$N(CH_3)_2$ | 1 | 0 | $C_3H_6$ | N | O |
| 19 | Cl | 3 | 3 | —$C_6H_2Br_3$ | 1 | 1 | $C_2H_4$ | S | S |
| 20 | Br | 3 | 3 | Cl | 2 | 2 | $C_3H_6$ | S | N |
| 21 | Br | 2 | 2 | Cl | 1 | 1 | $CH(CH_3)CH_2$ | N | N |
| 22 | Br | 4 | 4 | Cl | 1 | 1 | $CH(CH_3)CH_2CH_2$ | S | O |
| 23 | Br | 3 | 3 | F | 2 | 2 | $CH_2CH(CH_3)CH_2CH_2$ | O | N |
| 24 | Br | 1 | 1 | —$C_4H_9$ | 1 | 1 | $CH_2$ | N | N |
| 25 | Br | 1 | 1 | —$OC_4H_9$ | 1 | 1 | $C_2H_4$ | N | O |
| 26 | Br | 3 | 3 | — | 0 | 0 | $CH_2C(CH_2Cl)H$ | N | N |

Table I-continued

| Compound No. | Z | m | m' | A | i | i' | R | M | M' |
|---|---|---|---|---|---|---|---|---|---|
| 27 | Br | 3 | 3 | — | 0 | 0 | CH$_2$C(CH$_2$Cl)$_2$ | S | S |
| 28 | Br | 5 | 5 | — | 0 | 0 | CH$_2$C(CH$_2$Cl)H | S | N |
| 29 | Br | 2 | 2 | —CN | 1 | 1 | CH$_2$CH$_2$C(CH$_2$Br)H | S | O |
| 30 | Br | 2 | 2 | —NO$_2$ | 1 | 1 | CH$_2$(CHCl$_2$)H | O | N |
| 31 | Cl | 2 | 2 | —OCH$_3$ | 1 | 1 | CH$_2$C(CH$_2$Cl)H | O | N |
| 32 | Br | 3 | 3 | —OCH$_3$ | 1 | 1 | (CH$_2$)$_3$C(CH$_2$Cl)$_2$ | O | N |
| 33 | Br | 2 | 2 | —CH$_3$ | 1 | 1 | CH$_2$C(CH$_2$Cl)H | S | O |
| 34 | Br | 2 | 2 | F | 1 | 1 | CH$_2$C(CH$_2$Cl)$_2$ | S | N |
| 35 | Br | 2 | 2 | —N(CH$_3$)$_2$ | 1 | 1 | CH$_2$C(CHBr$_2$)H | N | N |
| 36 | Br | 2 | 2 | —C$_6$H$_5$ | 1 | 1 | (CH$_2$)$_2$C(CBr$_3$)H | S | N |
| 37 | Cl | 2 | 2 | —C$_6$H$_3$Br$_2$ | 1 | 1 | CH$_2$C(CH$_2$Cl)H | N | N |
| 38 | Br | 2 | 2 | —CH$_2$C$_6$H$_5$ | 1 | 1 | CH$_2$C(CCl$_3$)$_2$ | N | S |
| 39 | Br | 2 | 2 | —CH$_2$C$_6$H$_3$Br$_2$ | 1 | 1 | CH$_2$C(CH$_2$Cl)H | S | N |
| 40 | Cl | 3 | 3 | —C$_6$H$_3$Cl$_2$ | 1 | 1 | CH$_2$C(CH$_2$Cl)H | S | S |
| 41 | Br | 3 | 3 | F | 1 | 1 | CH$_2$C(CCl$_3$)$_2$ | N | N |
| 42 | Cl | 5 | 5 | — | 0 | 0 | CH$_2$C(CH$_2$Cl)H | N | O |
| 43 | Br | 4 | 4 | — | 0 | 0 | CH$_2$C(CH$_2$Cl)H | N | S |
| 44 | Br | 3 | 3 | —C$_6$H$_2$Br$_3$ | 1 | 1 | (CH$_2$)$_3$C(CH$_2$Cl)$_2$ | O | N |
| 45 | Br | 3 | 3 | — | 0 | 0 | CH$_2$C(CH$_2$Cl)HCH$_2$ | S | S |
| 46 | Br | 2 | 2 | — | 0 | 0 | CH$_2$C(CCl$_3$)H | N | S |
| 47 | Br | 4 | 4 | — | 0 | 0 | CH$_2$C(CHBr$_2$)H | N | N |
| 48 | Br | 3 | 3 | F | 2 | 2 | CH$_2$C(CH$_2$Cl)H | O | S |
| 49 | Br | 1 | 1 | —C$_4$H$_9$ | 1 | 1 | CH$_2$C(CH$_2$Cl)H | N | O |
| 50 | Br | 1 | 1 | —OC$_4$H$_9$ | 1 | 1 | (CH$_2$)$_3$C(CH$_2$Cl)H | N | N |
| 51 | Br | 2 | 2 | — | 0 | 0 | CH$_2$CH(OH)CH$_2$ | S | S |
| 52 | Br | 3 | 3 | — | 0 | 0 | CH$_2$CH(OH)CH$_2$ | N | N |
| 53 | Cl | 2 | 2 | — | 0 | 0 | CH$_2$CH(OH)CH$_2$ | S | N |
| 54 | Br | 2 | 2 | —CN | 1 | 1 | CH$_2$CH(OH)CH$_2$ | S | O |
| 55 | Br | 2 | 2 | —NO$_2$ | 1 | 1 | CH$_2$CH(OH)CH$_2$ | O | N |
| 56 | Br | 2 | 2 | —OCH$_3$ | 1 | 1 | CH$_2$CH(OH)CH$_2$ | N | N |
| 57 | Br | 3 | 3 | —OCH$_3$ | 1 | 1 | CH$_2$CH(OH)CH$_2$ | N | O |
| 58 | Br | 2 | 2 | —CH$_3$ | 1 | 1 | CH$_2$CH(OH)(CH$_3$ | S | S |
| 59 | Br | 2 | 2 | F | 1 | 1 | CH$_2$CH(OH)CH$_2$ | O | S |
| 60 | Br | 2 | 2 | —N(CH$_3$)$_2$ | 1 | 1 | CH$_2$CH(OH)CH$_2$ | N | N |
| 61 | Br | 2 | 2 | —C$_6$H$_5$ | 1 | 1 | CH$_2$CH(OH)CH$_2$ | S | S |
| 62 | Br | 2 | 2 | —C$_6$H$_3$Br$_2$ | 1 | 1 | CH$_2$CH(OH)CH$_2$ | N | N |
| 63 | Br | 2 | 2 | —CH$_2$C$_6$H$_5$ | 1 | 1 | CH$_2$CH(OH)CH$_2$ | S | N |
| 64 | Br | 2 | 2 | —CH$_2$C$_6$H$_3$Br$_2$ | 1 | 1 | CH$_2$CH(OH)CH$_2$ | N | S |
| 65 | Br | 3 | 3 | —C$_6$H$_3$Cl$_2$ | 1 | 1 | CH$_2$CH(OH)CH$_2$ | S | S |
| 66 | Cl | 3 | 3 | F | 1 | 1 | CH$_2$CH(OH)CH$_2$ | N | N |
| 67 | Cl | 2 | 2 | —CN | 2 | 2 | CH$_2$CH(OH)CH$_2$ | S | O |
| 68 | Br | 4 | 4 | — | 0 | 0 | CH$_2$CH(OH)CH$_2$ | N | O |
| 69 | Cl | 3 | 3 | —C$_6$H$_2$Br$_3$ | 1 | 1 | CH$_2$CH(OH)CH$_2$ | N | S |
| 70 | Cl | 3 | 3 | —NO$_2$ | 2 | 2 | CH$_2$CH(OH)CH$_2$ | S | S |
| 71 | Cl | 2 | 2 | —OCH$_3$ | 1 | 1 | CH$_2$CH(OH)CH$_2$ | N | N |
| 72 | Cl | 4 | 4 | —CH$_3$ | 1 | 1 | CH$_2$CH(OH)CH$_2$ | S | O |
| 73 | Cl | 3 | 3 | F | 2 | 2 | CH$_2$CH(OH)CH$_2$ | N | N |
| 74 | Br | 1 | 1 | —C$_4$H$_9$ | 1 | 1 | CH$_2$CH(OH)CH$_2$ | N | N |
| 75 | Br | 1 | 1 | —OC$_4$H$_9$ | 1 | 1 | CH$_2$CH(OH)CH$_2$ | O | N |
| 76 | Br | 2 | 2 | — | 0 | 0 | CH$_2$CH(CH$_2$OH)CH$_2$ | S | N |
| 77 | Br | 3 | 3 | — | 0 | 0 | CH$_2$CH(CH$_2$OH)CH$_2$ | S | O |
| 78 | Cl | 2 | 2 | — | 0 | 0 | CH$_2$CH(CH$_2$OH)CH$_2$ | N | N |
| 79 | Br | 2 | 2 | —CN | 1 | 1 | CH$_2$CH(CH$_2$OH)CH$_2$ | O | N |
| 80 | Br | 2 | 2 | —NO$_2$ | 1 | 1 | CH$_2$CH(CH$_2$OH)CH$_2$ | S | O |
| 81 | Br | 2 | 2 | —OCH$_3$ | 1 | 1 | CH$_2$CH(CH$_2$OH)CH$_2$ | O | N |
| 82 | Br | 3 | 3 | —OCH$_3$ | 1 | 1 | CH$_2$CH(CH$_2$OH)CH$_2$ | N | N |
| 83 | Br | 2 | 2 | —CH$_3$ | 1 | 1 | CH$_2$CH(CH$_2$OH)CH$_2$ | N | O |
| 84 | Br | 2 | 2 | F | 1 | 1 | CH$_2$CH(CH$_2$OH)CH$_2$ | S | S |
| 85 | Br | 2 | 2 | —N(CH$_3$)$_2$ | 1 | 1 | CH$_2$CH(CH$_2$OH)CH$_2$ | N | S |
| 86 | Br | 2 | 2 | —C$_6$H$_5$ | 1 | 1 | CH$_2$CH(CH$_2$OH)CH$_2$ | N | S |
| 87 | Br | 2 | 2 | —C$_6$H$_3$Br$_2$ | 1 | 1 | CH$_2$CH(CH$_2$OH)CH$_2$ | N | N |
| 88 | Br | 2 | 2 | —CH$_2$C$_6$H$_5$ | 1 | 1 | CH$_2$CH(CH$_2$OH)CH$_2$ | S | S |
| 89 | Br | 2 | 2 | —CH$_2$C$_6$H$_3$Br$_2$ | 1 | 1 | CH$_2$CH(CH$_2$OH)CH$_2$ | N | N |
| 90 | Br | 3 | 3 | —C$_6$H$_3$Cl$_2$ | 1 | 1 | CH$_2$CH(CH$_2$OH)CH$_2$ | N | N |
| 91 | Cl | 3 | 3 | F | 1 | 1 | CH$_2$CH(CH$_2$OH)CH$_2$ | O | N |
| 92 | Cl | 2 | 2 | —CN | 2 | 2 | CH$_2$CH(CH$_2$OH)CH$_2$ | S | N |
| 93 | Br | 4 | 4 | — | 0 | 0 | CH$_2$CH(CH$_2$OH)CH$_2$ | O | N |
| 94 | Cl | 3 | 3 | —C$_6$H$_2$Br$_3$ | 1 | 1 | CH$_2$CH(CH$_2$OH)CH$_2$ | S | S |
| 95 | Cl | 3 | 3 | —NO$_2$ | 2 | 2 | CH$_2$CH(CH$_2$OH)CH$_2$ | N | N |
| 96 | Cl | 2 | 2 | —OCH$_3$ | 1 | 1 | CH$_2$CH(CH$_2$OH)CH$_2$ | O | N |
| 97 | Cl | 4 | 4 | —CH$_3$ | 1 | 1 | CH$_2$CH(CH$_2$OH)CH$_2$ | N | S |
| 98 | Cl | 3 | 3 | F | 2 | 2 | CH$_2$CH(CH$_2$OH)CH$_2$ | O | O |
| 99 | Br | 1 | 1 | —C$_4$H$_9$ | 1 | 1 | CH$_2$CH(CH$_2$OH)CH$_2$ | O | N |
| 100 | Br | 1 | 1 | —OC$_4$H$_9$ | 1 | 1 | CH$_2$CH(CH$_2$OH)CH$_2$ | N | N |
| 101 | Br | 2 | 2 | — | 0 | 0 | CH$_2$OCH$_2$ | O | N |
| 102 | Br | 3 | 3 | — | 0 | 0 | CH$_2$OCH$_2$ | S | S |
| 103 | Cl | 2 | 2 | — | 0 | 0 | (CH$_2$)$_6$O(CH$_2$)$_6$ | S | N |
| 104 | Br | 2 | 2 | —CN | 1 | 1 | (CH$_2$)$_2$O(CH$_2$)$_2$ | O | O |
| 105 | Br | 2 | 2 | —NO$_2$ | 1 | 1 | CH$_2$OCH$_2$ | O | N |
| 106 | Br | 2 | 2 | —OCH$_3$ | 1 | 1 | (CH$_2$)$_3$O(CH$_2$)$_3$ | N | N |
| 107 | Br | 3 | 3 | —OCH$_3$ | 1 | 1 | (CH$_2$)$_2$O(CH$_2$)$_5$ | N | O |
| 108 | Br | 2 | 2 | —CH$_3$ | 1 | 1 | CH$_2$OCH$_2$ | S | S |
| 109 | Br | 2 | 2 | F | 1 | 1 | CH$_2$OCH$_2$ | O | S |
| 110 | Br | 2 | 2 | —N(CH$_3$)$_2$ | 1 | 1 | CH$_2$OCH$_2$ | N | N |
| 111 | Br | 2 | 2 | —C$_6$H$_5$ | 1 | 1 | CH$_2$OCH$_2$ | S | N |
| 112 | Br | 2 | 2 | —C$_6$H$_3$Br$_2$ | 1 | 1 | (CH$_2$)$_6$O(CH$_2$)$_4$ | N | N |
| 113 | Br | 2 | 2 | —CH$_2$C$_6$H$_5$ | 1 | 1 | CH$_2$OCH$_2$ | N | S |
| 114 | Br | 2 | 2 | —CH$_2$C$_6$H$_3$Br$_2$ | 1 | 1 | (CH$_2$)$_3$O(CH$_2$)$_3$ | N | N |
| 115 | Br | 3 | 3 | —C$_6$H$_3$Cl$_2$ | 1 | 1 | CH$_2$OCH$_2$ | S | N |
| 116 | Cl | 3 | 3 | F | 1 | 1 | CH$_2$OCH$_2$ | N | N |
| 117 | Cl | 2 | 2 | —CN | 2 | 2 | CH$_2$OCH$_2$ | O | N |
| 118 | Br | 4 | 4 | — | 0 | 0 | (CH$_2$)$_2$OCH$_2$ | S | N |

Table I-continued

| Compound No. | Z | m | m' | A | i | i' | R | M | M' |
|---|---|---|---|---|---|---|---|---|---|
| 119 | Cl | 3 | 3 | —C₆H₂Br₃ | 1 | 1 | CH₂OCH₂ | N | O |
| 120 | Cl | 3 | 3 | —NO₂ | 2 | 2 | (CH₂)₂O(CH₂)₂ | S | S |
| 121 | Cl | 2 | 2 | —OCH₃ | 1 | 1 | CH₂OCH₂ | N | S |
| 122 | Cl | 4 | 4 | —CH₃ | 1 | 1 | CH₂OCH₂ | N | N |
| 123 | Cl | 3 | 3 | F | 2 | 2 | CH₂OCH₂ | S | O |
| 124 | Br | 1 | 1 | —C₄H₉ | 1 | 1 | CH₂OCH₂ | O | N |
| 125 | Br | 1 | 1 | —OC₄H₉ | 1 | 1 | CH₂OCH₂ | N | N |
| 126 | Br | 2 | 2 | — | 0 | 0 | CH₂(C₆H₄)CH₂ | S | N |
| 127 | Br | 3 | 3 | — | 0 | 0 | CH₂(C₆H₂Br₂)CH₂ | S | S |
| 128 | Cl | 2 | 2 | — | 0 | 0 | CH₂(C₆H₂Cl₂)CH₂ | O | S |
| 129 | Br | 3 | 3 | —CN | 1 | 1 | CH₂(C₆Br₄)CH₂ | N | N |
| 130 | Br | 2 | 2 | —NO₂ | 1 | 1 | CH₂(C₆Cl₄)CH₂ | N | O |
| 131 | Br | 2 | 2 | —OCH₃ | 1 | 1 | CH₂(C₆H₄)CH₂ | S | S |
| 132 | Br | 3 | 3 | —OCH₃ | 1 | 1 | CH₂(C₆HBr₃)CH₂ | O | S |
| 133 | Br | 2 | 2 | —CH₃ | 1 | 1 | CH₂(C₆H₂Br₂)CH₂ | N | N |
| 134 | Br | 2 | 2 | F | 1 | 1 | CH₂(C₆Br₄)CH₂ | S | S |
| 135 | Br | 2 | 2 | —N(CH₃)₂ | 1 | 1 | CH₂(C₆HBr₃)CH₂ | N | N |
| 136 | Br | 2 | 2 | —C₆H₅ | 1 | 1 | CH₂(C₆H₄)CH₂ | S | N |
| 137 | Br | 2 | 2 | —C₆H₃Br₂ | 1 | 1 | CH₂(C₆H₄)CH₂ | S | N |
| 138 | Br | 2 | 2 | —CH₂C₆H₅ | 1 | 1 | CH₂(C₆H₂Br₂)CH₂ | S | S |
| 139 | Br | 2 | 2 | —CH₂C₆H₃Br₂ | 1 | 1 | CH₂(C₆HBr₃)CH₂ | N | N |
| 140 | Br | 3 | 3 | —C₆H₃Cl₂ | 1 | 1 | CH₂(C₆Cl₄)CH₂ | N | N |
| 141 | Cl | 3 | 3 | F | 1 | 1 | CH₂(C₆H₄)CH₂ | N | O |
| 142 | Cl | 2 | 2 | —CN | 2 | 2 | CH₂(C₆HBr₃)CH₂ | N | O |
| 143 | Br | 4 | 4 | — | 0 | 0 | CH₂(C₆H₄)CH₂ | S | S |
| 144 | Cl | 3 | 3 | —C₆H₂Br₃ | 1 | 1 | CH₂(C₆Br₄)CH₂ | S | O |
| 145 | Cl | 3 | 3 | —NO₂ | 2 | 2 | CH₂(C₆H₄)CH₂ | S | N |
| 146 | Cl | 2 | 2 | —OCH₃ | 1 | 1 | CH₂(C₆H₄)CH₂ | N | N |
| 147 | Cl | 4 | 4 | —CH₃ | 1 | 1 | CH₂(C₆H₄)CH₂ | S | O |
| 148 | Cl | 3 | 3 | F | 2 | 2 | CH₂(C₆H₄)CH₂ | O | N |
| 149 | Br | 1 | 1 | —C₄H₉ | 1 | 1 | CH₂(C₆Br₄)CH₂ | O | N |
| 150 | Br | 1 | 1 | —OC₄H₉ | 1 | 1 | CH₂(C₆Br₄)CH₂ | N | N |
| 151 | Br | 2 | 2 | — | 0 | 0 | CH₂—C(O)—CH₂ | N | N |
| 152 | Br | 2 | 2 | — | 0 | 0 | CH₂—C(O)—CH₂ | S | S |
| 153 | Cl | 2 | 2 | — | 0 | 0 | CH₂—C(O)—CH₂ | N | S |
| 154 | Br | 2 | 2 | —CN | 1 | 1 | CH₂—C(O)—CH₂ | O | S |
| 155 | Br | 2 | 2 | —NO₂ | 1 | 1 | CH₂—C(O)—CH₂ | N | O |
| 156 | Br | 2 | 2 | —OCH₃ | 1 | 1 | CH₂—C(O)—CH₂ | N | N |
| 157 | Br | 3 | 3 | —OCH₃ | 1 | 1 | CH₂—C(O)—CH₂ | N | O |
| 158 | Br | 2 | 2 | —CH₃ | 1 | 1 | CH₂—C(O)—CH₂ | S | S |
| 159 | Br | 2 | 2 | F | 1 | 1 | CH₂—C(O)—CH₂ | O | S |
| 160 | Br | 2 | 2 | —N(CH₃)₂ | 1 | 1 | CH₂—C(O)—CH₂ | N | N |
| 161 | Br | 2 | 2 | —C₆H₅ | 1 | 1 | CH₂—C(O)—CH₂ | S | S |
| 162 | Br | 2 | 2 | —C₆H₃Br₂ | 1 | 1 | CH₂—C(O)—CH₂ | N | N |
| 163 | Br | 2 | 2 | —CH₂C₆H₅ | 1 | 1 | CH₂—C(O)—CH₂ | N | S |
| 164 | Br | 2 | 2 | —CH₂C₆H₃Br₂ | 1 | 1 | CH₂—C(O)—CH₂ | N | S |
| 165 | Br | 3 | 3 | —C₆H₃Cl₂ | 1 | 1 | CH₂—C(O)—CH₂ | S | N |
| 166 | Cl | 3 | 3 | F | 1 | 1 | CH₂—C(O)—CH₂ | O | N |
| 167 | Cl | 2 | 2 | —CN | 2 | 2 | CH₂—C(O)—CH₂ | S | N |
| 168 | Br | 4 | 4 | — | 0 | 0 | CH₂—C(O)—CH₂ | N | N |
| 169 | Cl | 3 | 3 | —C₆H₂Br₃ | 1 | 1 | CH₂—C(O)—CH₂ | N | O |
| 170 | Cl | 3 | 3 | —NO₂ | 2 | 2 | CH₂—C(O)—CH₂ | O | S |
| 171 | Cl | 2 | 2 | —OCH₃ | 1 | 1 | CH₂—C(O)—CH₂ | N | S |
| 172 | Cl | 4 | 4 | —CN | 1 | 1 | CH₂—C(O)—CH₂ | N | N |
| 173 | Cl | 3 | 3 | F | 2 | 2 | CH₂—C(O)—CH₂ | N | O |
| 174 | Br | 1 | 1 | —C₄H₉ | 1 | 1 | CH₂—C(O)—CH₂ | O | N |
| 175 | Br | 1 | 1 | —OC₄H₉ | 1 | 1 | CH₂—C(O)—CH₂ | N | N |
| 176 | Br | 2 | 2 | — | 0 | 0 | —CH₂C(C₆H₅)H— | N | N |
| 177 | Br | 2 | 2 | — | 0 | 0 | —CH₂C(C₆H₅)H— | N | O |
| 178 | Cl | 2 | 2 | — | 0 | 0 | —CH₂C(C₆H₅)H— | S | N |
| 179 | Br | 2 | 2 | —CN | 1 | 1 | —CH₂C(C₆H₅)H— | N | N |
| 180 | Br | 2 | 2 | —NO₂ | 1 | 1 | —CH₂C(C₆H₅)H— | S | S |
| 181 | Br | 2 | 2 | —OCH₃ | 1 | 1 | —CH₂C(C₆H₅)H— | S | N |
| 182 | Br | 3 | 3 | —OCH₃ | 1 | 1 | —CH₂C(C₆H₅)H— | O | S |
| 183 | Br | 2 | 2 | —CH₃ | 1 | 1 | —CH₂C(C₆H₅)H— | N | S |
| 184 | Br | 2 | 2 | F | 1 | 1 | —CH₂C(C₆H₅)H— | N | O |
| 185 | Br | 2 | 2 | —N(CH₃)₂ | 1 | 1 | —CH₂C(C₆H₅)H— | N | S |
| 186 | Br | 2 | 2 | —C₆H₅ | 1 | 1 | —CH₂C(C₆H₅)H— | S | N |
| 187 | Br | 2 | 2 | —C₆H₃Br₂ | 1 | 1 | —CH₂C(C₆H₅)H— | S | N |
| 188 | Br | 2 | 2 | —CH₂C₆H₅ | 1 | 1 | —CH₂C(C₆H₅)H— | S | N |
| 189 | Br | 2 | 2 | —CH₂C₆H₃Br₂ | 1 | 1 | —CH₂C(C₆H₅)H— | N | N |
| 190 | Br | 3 | 3 | —C₆H₃Cl₂ | 1 | 1 | —CH₂C(C₆H₅)H— | S | S |
| 191 | Cl | 3 | 3 | F | 1 | 1 | —CH₂C(C₆H₅)H— | N | N |
| 192 | Cl | 2 | 2 | —CN | 2 | 2 | —CH₂C(C₆H₅)H— | S | O |
| 193 | Br | 4 | 4 | — | 0 | 0 | —CH₂C(C₆H₅)H— | S | S |
| 194 | Cl | 3 | 3 | —C₆H₂Br₃ | 1 | 1 | —CH₂C(C₆H₅)H— | O | N |
| 195 | Cl | 3 | 3 | —NO₂ | 2 | 2 | —CH₂C(C₆H₅)H— | N | N |
| 196 | Cl | 2 | 2 | —OCH₃ | 1 | 1 | —CH₂C(C₆H₅)H— | O | N |
| 197 | Cl | 4 | 4 | —CH₃ | 1 | 1 | —CH₂C(C₆H₅)H— | S | O |
| 198 | Cl | 3 | 3 | F | 2 | 2 | —CH₂C(C₆H₅)H— | S | N |
| 199 | Br | 1 | 1 | —C₄H₉ | 1 | 1 | —CH₂C(C₆H₅)H— | S | N |
| 200 | Br | 1 | 1 | —OC₄H₉ | 1 | 1 | —CH₂C(C₆H₅)H— | N | N |
| 201 | Br | 2 | 2 | — | 0 | 0 | 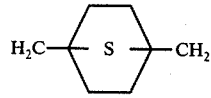 | N | N |

Table I-continued
| Compound No. | Z | m | m' | A | i | i' | R | M | M' |
|---|---|---|---|---|---|---|---|---|---|
| 202 | Br | 2 | 2 | — | 0 | 0 | 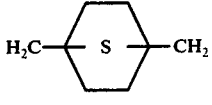 | S | S |
| 203 | Cl | 2 | 2 | — | 0 | 0 | 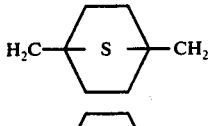 | N | S |
| 204 | Br | 2 | 2 | —CN | 1 | 1 | 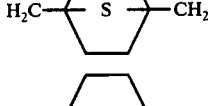 | S | O |
| 205 | Br | 2 | 2 | —NO$_2$ | 1 | 1 | 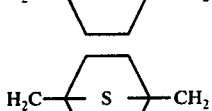 | O | N |
| 206 | Br | 2 | 2 | —OCH$_3$ | 1 | 1 | 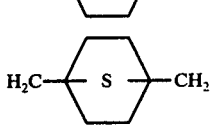 | N | N |
| 207 | Br | 3 | 3 | —OCH$_3$ | 1 | 1 | 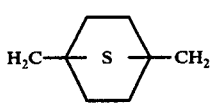 | O | N |
| 208 | Br | 2 | 2 | —CH$_3$ | 1 | 1 | 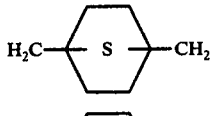 | S | S |
| 209 | Br | 2 | 2 | F | 1 | 1 | 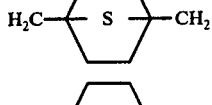 | O | S |
| 210 | Br | 2 | 2 | —N(CH$_3$)$_2$ | 1 | 1 | 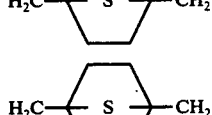 | N | N |
| 211 | Br | 2 | 2 | —C$_6$H$_5$ | 1 | 1 | 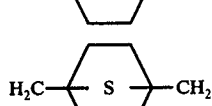 | S | S |
| 212 | Br | 2 | 2 | —C$_6$H$_3$Br$_2$ | 1 | 1 | 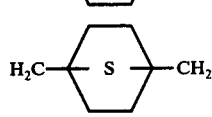 | N | N |
| 213 | Br | 2 | 2 | —CH$_2$C$_6$H$_5$ | 1 | 1 | 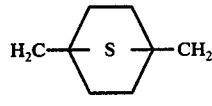 | N | S |
| 214 | Br | 2 | 2 | —CH$_2$C$_6$H$_3$Br$_2$ | 1 | 1 | 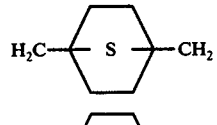 | N | S |
| 215 | Br | 3 | 3 | —C$_6$H$_3$Cl$_2$ | 1 | 1 | 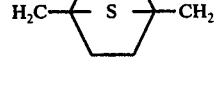 | S | S |
| 216 | Cl | 3 | 3 | F | 1 | 1 | | N | N |
| 217 | Cl | 2 | 2 | —CN | 2 | 2 |  | N | O |

Table I-continued

| Compound No. | Z | m | m' | A | i | i' | R | M | M' |
|---|---|---|---|---|---|---|---|---|---|
| 218 | Br | 4 | 4 | — | 0 | 0 | H₂C—⟨S⟩—CH₂ | N | S |
| 219 | Cl | 3 | 3 | —C₆H₂Br₃ | 1 | 1 | H₂C—⟨S⟩—CH₂ | O | N |
| 220 | Cl | 3 | 3 | —NO₂ | 2 | 2 | H₂C—⟨S⟩—CH₂ | S | S |
| 221 | Cl | 2 | 2 | —OCH₃ | 1 | 1 | H₂C—⟨S⟩—CH₂ | S | N |
| 222 | Cl | 4 | 4 | —CH₃ | 1 | 1 | H₂C—⟨S⟩—CH₂ | N | N |
| 223 | Cl | 3 | 3 | F | 2 | 2 | H₂C—⟨S⟩—CH₂ | O | S |
| 224 | Br | 1 | 1 | —C₄H₉ | 1 | 1 | H₂C—⟨S⟩—CH₂ | N | O |
| 225 | Br | 1 | 1 | —OC₄H₉ | 1 | 1 | H₂C—⟨S⟩—CH₂ | N | N |

In general, the halogenated aryl compounds are prepared by reacting a halogenated phenol, thiophenol or aryl amine with a halogenated alkane at elevated temperatures in the presence of a basic material such as alkali metal hydroxides, carbonates, bicarbonates, oxides and hydrides. The preferred alkali metals are potassium and sodium. When one desires to increase, for example, ease of handling the reaction mass, solvents such as ketones (e.g. acetone, methyl ethyl ketone, and methyl iso-butyl ketone), alcohols (e.g. methanol, ethanol, iso-propyl alcohol, butyl alcohol and glycols), aqueous solvents (e.g. water, a mixture of water and alcohol and a mixture of water and ketone), and polar aprotic solvents such as dimethylformamide (DMF), dimethyl sulfoxide (DMSO) and ethers such as tetrahydrofuran (THF), can be employed. The desired end product i.e., the halogenated aryl compound, can be recovered from the reaction mass via various methods such as distillation or crystallization. Where the end product requires recovery via crystallization, various aromatic solvents such as benzene, toluene, xylene, dichlorobenzene and the like can be used.

Specifically, the symmetrical halogenated aryl compounds are prepared, for example, according to the following reactions:

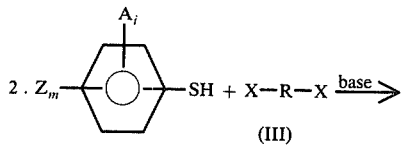

(III)

-continued

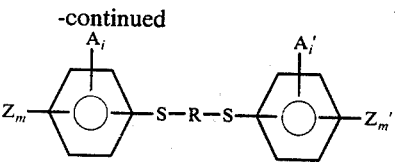

In the above reaction, X is halogen, preferably chlorine and R is the same as defined herein. Where m and m' and i and i' are different integers, then equivalent molar portions of the particular halogenated phenol, thiophenol or aryl amine are used with equivalent portions of dissimilar halogenated phenol, thiophenol or aryl amine.

The unsymmetrical halogenated aryl compounds are prepared, for example, according to the following reactions:

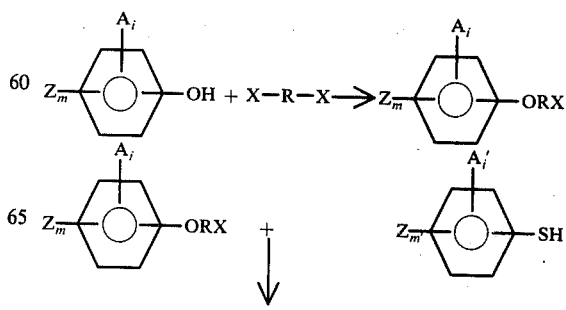

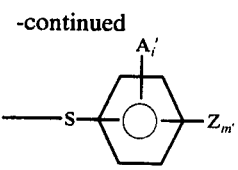

In the above reaction, X and R are the same as mentioned above.

The above reactions are conducted at temperatures ranging from the freezing point of the initial reaction mass to the boiling point thereof. Preferably the temperatures are from about 40° C to about 200° C and more preferably from about 50° C to about 175° C. It is to be understood that the reaction can be conducted under sub-atmospheric (e.g. 1/10–8/10 atmospheres), atmospheric or super-atmospheric (e.g. 1.5–10 atmospheres) pressure. Preferably, the reaction is carried out at atmospheric pressure.

The above-described processes can be carried out with conventional, readily available chemical processing equipment. For example, a conventional glass-lined vessel provided with heat transfer means, a reflux condenser and a mechanical stirrer can be advantageously utilized in practicing any of the preferred embodiments of the invention described in the examples set forth herein.

The halogenated aryl compounds falling within Formula I having unique utility in the field of ABS plastics and have been found to function as flame retardants therefor. The incorporation of these compounds in ABS results in ABS plastic compositions characterized by being effectively flame retarded and possessing substantially the same properties as ABS without such incorporation.

The disadvantages in the utilization of various prior art materials as flame retardants for ABS include, without limitation, factors such as thermal migration, heat instability, light instability, non-biodegradable, toxicity, discoloration and the large amounts employed in order to be effective. However, the present invention compounds, when incorporated into ABS, provide ABS plastic compositions which possess highly desirable chemical, physical and mechanical properties and which compositions substantially overcome the prior art disadvantages.

Furthermore, these compounds are quite economical and can easily be incorporated into ABS without being degraded or decomposed as a result of blending or processing operations.

It is to be understood that the term ABS as used herein means acrylonitrile-butadiene-styrene copolymers which are thermoplastic polymers produced, for example (but without limitation), by blending a styrene/acrylonitrile copolymer with butadiene-based rubber, or by grafting butadiene-based rubber (usually polybutadiene) with styrene/acrylonitrile chains, or by copolymerization of styrene, acrylonitrile and butadiene monomers.

EXAMPLE I

Approximately 600 ml of N, N-dimethylformamide, 94.5g (0.5 mole) of 4-bromothiophenol, and 28g (0.5 mole) of KOH pellets are charged to a 3000 ml reaction flask equipped with a mechanical stirrer, thermometer, reflux condenser and addition funnel. The resultant mixture is heated to about 100° C at which temperature there results a yellow solution.

While maintaining this solution at about 100° C, there is added via the addition funnel a solution of approximately 204g (0.5 mole) of 1-(2,4,6-tribromophenoxy)-3-chloropropane, in 600 ml of N,N-dimethylformamide, over a period of 60 minutes. The resulting mixture is maintained at about 100° C for approximately 120 minutes after the 60 minute addition period.

After this 120 minute period, the mixture is allowed to cool to room temperature (about 20° C - 25° C) and the resultant mixture diluted with 1000 ml of water. The resultant dark solid material is isolated by suction filtration. Crystallization from benzene-ethanol yields a substantially white crystalline solid.

Utilizing infrared spectrometer and bromine analysis via Parr bomb, the solid is analyzed and shows that there is produced a compound having the following structural formula:

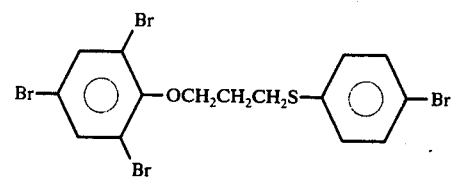

EXAMPLE II

Approximately 600 ml of N, N-dimethylformamide, 94.5g (0.5 mole) of 4-bromothiophenol, and 28g (0.5 mole) of KOH pellets are charged to a 3000 ml reaction flask equipped with a mechanical stirrer, thermometer, reflux condenser and addition funnel. The resultant mixture is heated to about 100° C at which temperature there results a yellow solution.

While maintaining this solution at about 100° C, there is added via the addition funnel a solution of approximately 219g (0.5 mole) of 1-(2,4,6-tribromophenoxy)-2-bromoethane, in 600 ml of N, N-dimethylformamide, over a period of 60 minutes. The resulting mixture is maintained at about 100° C for approximately 120 minutes after the 60 minute addition period.

After this 120 minute period, the mixture is allowed to cool to room temperature (about 20° C - 25° C) and the resultant mixture diluted with 1000 ml of water. The resultant dark solid material is isolated by suction filtration. Crystallization from benzene-ethanol yields a substantially white crystalline solid.

Utilizing infrared spectrometer and bromine analysis via Parr bomb, the solid is analyzed and shows that there if produced a compound having the following structural formula:

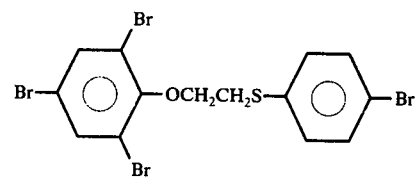

EXAMPLE III

Approximately 2000 milliliters (ml) of N, N-dimethylformamide, 189g (1.0 mole) of 4-bromothiophenol and 40g (1.0 mole) of sodium hydroxide pellets are charged to a 5000 ml reaction flask equipped with a mechanical stirrer, thermometer, reflux condenser and addition funnel. The resultant mixture is heated to about 130° C at which temperature there results a brown solution.

While maintaining this solution at about 130° C, there is added dropwise via the addition funnel 94g (0.5 mole) of 1,2-dibromoethane over a period of 30 minutes. The resulting mixture is maintained at about 130° C for approximately 90 minutes after the 30 minute dropwise addition period.

After this 90 minute period, the mixture is permitted to cool to room temperature (about 25° C). The mixture is then diluted with 1000 ml of a 5% aqueous sodium hydroxide solution. The resultant solid material is isolated by suction filtration. The filter cake material is then washed twice with 500 ml portions, of water and finally with 500 ml of cold ethanol. A substantially white crystalline solid is obtained after drying at 100° C.

Utilizing infrared spectrometer and bromine analysis via Parr bomb, the solid is analyzed and shows that there is produced a compound having the following structural formula:

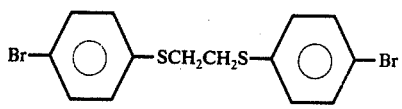

EXAMPLE IV

Approximately 600 ml of N, N-dimethylformamide, 86g (0.5 mole) of 4-bromoaniline, and 27g (0.25 mole) of sodium carbonate are charged to a 3000 ml reaction flask equipped with a mechanical stirrer, thermometer, reflux condenser and addition funnel. The resultant mixture is heated to about 100° C at which temperature there results a yellow solution.

While maintaining this solution at about 100° C, there is added via the addition funnel a solution of approximately 204g (0.5 mole) of 1-(2,4,6-tribromophenoxy)-3-chloropropane in 600 ml of N, N-dimethylformamide, over a period of 60 minutes. The resulting mixture is maintained at about 100° C for approximately 120 minutes after the 60 minute addition period.

After this 120 minute period, the mixture is allowed to cool to room temperature (about 20° C - 25° C) and the resultant mixture diluted with 1000 ml of water. The resultant dark solid material is isolated by suction filtration. Crystallization from benzene-ethanol yields a substantially white crystalline solid.

Utilizing infrared spectrometer and bromine analysis via Parr bomb, the solid is analyzed and shows that there is produced a compound having the following structural formula:

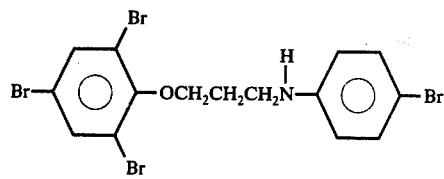

EXAMPLE V

Approximately 2000 milliliters (ml) of N, N-dimethylformamide, 251g (1.0 mole) of 2,4-dibromoaniline and 53g (0.5 mole) of sodium carbonate are charged to a 5000 ml reaction flask equipped with a mechanical stirrer, thermometer, reflux condenser and addition funnel. The resultant mixture is heated to about 130° C at which temperature there results a brown solution.

While maintaining this solution at about 130° C, there is added dropwise via the addition funnel 101g (0.5 mole) of 1,2-dibromoethane over a period of 30 minutes. The resulting mixture is maintained at about 130° C for approximately 90 minutes after the 30 minute dropwise addition period.

After this 90 minute period, the mixture is permitted to cool to room temperature (about 25° C). The mixture is then diluted with 1000 ml of a 5% aqueous sodium hydroxide solution. The resultant solid material is isolated by suction filtration. The filter cake material is then washed twice with 500 ml portions of water and finally with 500 ml of cold ethanol. A substantially white crystalline solid is obtained after crystallization from chloroform and drying at 100° C.

Utilizing infrared spectrometer and bromine analysis via Parr bomb, the solid is analyzed and shows that there is produced a compound having the following structural formula:

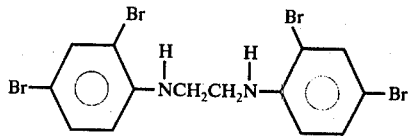

EXAMPLE VI

Approximately 200 ml of N, N-dimethylformamide, 34g (0.10 mole) of pentachlorophenol and 4.0g (0.10 mole) of sodium hydroxide pellets are charged to a 500 ml reaction flask equipped with a mechanical stirrer, thermometer, reflux condenser, and stopper. The resultant mixture is heated to 130° C at which temperature there results a brown solution.

While maintaining this solution at about 130° C, there is added as rapidly as possible 57g (0.10 mole) of 3-pentachloroanilino-2,2-bis(chloromethyl)-1-propyl-p-toluenesulfonate as a solid. The resulting mixture is maintained at about 130° C for approximately 120 minutes after the solid addition.

After this 120 minute period, the mixture is allowed to cool to room temperature (about 20° C - 25° C), diluted with 200 ml of a 5% aqueous sodium hydroxide solution, and the resultant solid is recovered by filtration. The filter cake marterial is washed twice with 200 ml portions of water and finally with 100 ml of cold ethanol. The material yields a substantially white crystalline solid upon drying.

Utilizing infrared spectrometer and chlorine analysis via Parr bomb, the solid is analyzed and shows that there is produced a compound having the following structural formula:

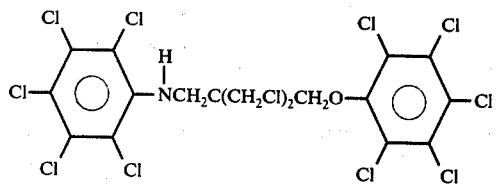

EXAMPLE VII

Approximately 200 ml of N, N-dimethylformamide, 28g (0.1 mole) of 2,6-dibromo-4-cyanophenol and 5.6g (0.1 mole) of KOH pellets are charged to a 1000 ml reaction flask equipped with a mechanical stirrer, thermometer, reflux condenser and addition funnel. The resultant mixture is heated to about 100° C at which temperature there results a brown solution.

While maintaining this solution at about 100° C, there is added via the addition funnel a solution of approximately 43g (0.1 mole) of 1-(2,6-dibromo-4-cyanothiophenoxy)-3-bromo-2-propanol in 200 ml of N, N-dimethylformamide, over a period of 60 minutes. The resulting mixture is maintained at about 100° C for approximately 120 minutes after the 60 minute addition period.

After this 120 minute period, the mixture is allowed to cool to room temperature (about 20° C – 25° C) and the resultant mixture diluted with 400 ml of water. The resultant dark solid material material is isolated by suction filtration. Crystallization from toluene yields a substantially white crystalline solid.

Utilizing infrared spectrometer and bromine analysis via Parr bomb, the solid is analyzed and shows that there is produced a compound having the following structural formula:

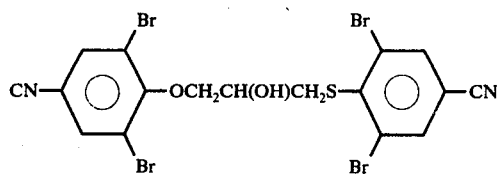

EXAMPLE VIII

Approximately 200 ml of N,N-dimethylformamide, 27g (0.1 mole) of 2,4-dibromothiophenol and 5.6g (0.1 mole) of KOH pellets are charged to a 1000 ml reaction flask equipped with a mechanical stirrer, thermometer, reflux condenser and addition funnel. The resultant mixture is heated to about 100° C at which temperature there results a yellow solution.

While maintaining this solution at about 100° C, there is added via the addition funnel a solution of approximately 42g (0.1 mole) of 3-(2,4-dibromoanilino)-2-(bromomethyl)-2-methyl-1-propanol in 200 ml of N,N-dimethylformamide, over a period of 60 minutes. The resulting mixture is maintained at about 100° C for approximately 120 minutes after the 60 minute addition period.

After this 120 minute period, the mixture is allowed to cool to room temperature (about 20° C – 25° C) and the resultant mixture diluted with 400 ml of water. The resultant dark solid material is isolated by suction filtration. Crystallization from chloroform yields a substantially white crystalline solid.

Utilizing infrared spectrometer and bromine analysis via Parr bomb, the solid is analyzed and shows that there is produced a compound having the following structural formula:

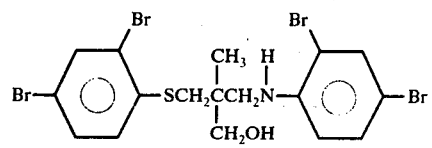

EXAMPLE IX

Approximately 2000 milliliters (ml) of N,N-dimethylformamide, 268g (1.0 mole) of 2,4-dibromoaniline and 53g (0.5 mole) of sodium carbonate are charged to a 5000 ml reaction flask equipped with a mechanical stirrer, thermometer, reflux condenser and addition funnel. The resultant mixture is heated to about 130° C at which temperature there results a brown solution.

While maintaining this solution at about 130° C, there is added dropwise via the addition funnel 115g (0.5 mole) of bis(chloromethyl)ether over a period of 30 minutes. The resulting mixture is maintained at about 130° C for approximately 90 minutes after the 30 minute dropwise addition period.

After this 90 minute period, the mixture is permitted to cool to room temperature (about 25° C). The mixture is then diluted with 1000 ml of a 5% aqueous sodium hydroxide solution. The resultant solid material is isolated by suction filtration. The filter cake material is then washed twice with 500 ml portions of water and finally with 500 ml of cold ethanol. A substantially white crystalline solid is obtained after drying at 100° C.

Utilizing infrared spectrometer and bromine analysis via Parr bomb, the solid is analyzed and shows that there is produced a compound having the following structural formula:

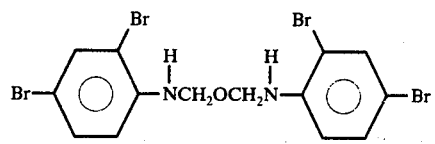

EXAMPLE X

Approximately 200 ml of N,N-dimethylformamide, 27g (0.1 mole) of 2,4-dibromothiophenol and 4g (0.1 mole) of sodium hydroxide pellets are charged to a 1000 ml reaction flask equipped with a mechanical stirrer, thermometer, reflux condenser, and stopper. The resultant mixture is heated to 130° C at which temperature there results a brown solution.

While maintaining this solution at about 130° C, there is added as rapidly as possible 39g (0.1 mole) of 1-(2,4,-dibromoanilinomethyl)-4-chloromethylbenzene as a solid. The resulting mixture is maintained at about 130° C for approximately 120 minutes after the solid addition.

After this 120 minute period, the mixture is allowed to cool to room temperature (about 20° C – 25° C), diluted with 200 ml of a 5% aqueous sodium hydroxide solution, and the resultant solid is recovered by filtration. The filter cake material is washed twice with 200 ml portions of water and finally with 100 ml of cold acetone. The material yields a substantially white crystalline solid upon drying.

Utilizing infrared spectrometer and bromine analysis via Parr bomb, the solid is analyzed and shows that there is produced a compound having the following structural formula:

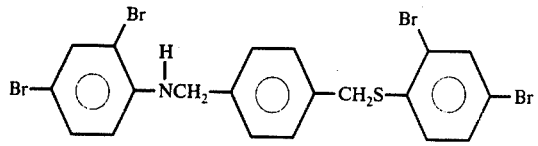

EXAMPLE XI

Approximately 200 milliliters (ml) of N,N-dimethylformamide, 27g (0.1 mole) of 2,4-dibromothiophenol and 4g (0.1 mole) of sodium hydroxide pellets are charged to a 1000 ml reaction flask equipped with a mechanical stirrer, thermometer, reflux condenser and addition funnel. The resultant mixture is heated to about 130° C at which temperature there results a brown solution.

While maintaining this solution at about 130° C, there is added dropwise via the addition funnel 6.3g (0.05 mole) of 1,3-dichloroacetone over a period of 30 minutes. The resulting mixture is maintained at about 130° C for approximately 90 minutes after the 30 minute dropwise addition period.

After this 90 minute period, the mixture is permitted to cool to room temperature (about 25° C). The mixture is then diluted with 200 ml of cold 5% aqueous sodium hydroxide solution. The resultant solid material is isolated by suction filtration. The filter cake material is then washed twice with 200 ml portions of water and finally with 50 ml of cold ethanol. A substantially white crystalline solid is obtained after drying at 100° C.

Utilizing infrared spectrometer and bromine analysis via Parr bomb, the solid is analyzed and shows that there is produced a compound having the following structural formula:

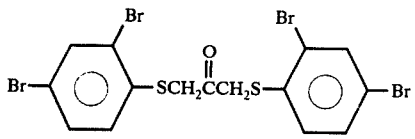

EXAMPLE XII

Approximately 200 ml of N,N-dimethylformamide, 18g (0.1 mole) of 2,4-dichlorothiophenol and 4.0g (0.1 mole) of sodium hydroxide pellets are charged to a 1000 ml reaction flask equipped with a mechanical stirred, thermometer, reflux condenser, and stopper. The resultant mixture is heated to 130° C at which temperature there results a brown solution.

While maintaining this solution at about 130° C, there is added as rapidly as possible 35g (0.1 mole) of 1-bromo-1-phenyl-2-(2,4-dichlorophenoxy)ethane as a solid. The resulting mixture is maintained at about 130° C for approximately 120 minutes after the solid addition.

After this 120 minute period, the mixture is allowed to cool to room temperature (about 20° C - 25° C), diluted with 200 ml of a 5% aqueous sodium hydroxide solution, and the resultant solid is recovered by filtration. The filter cake material is washed twice with 200 ml portions of water and finally with 100 ml of cold acetone. The material yields a substantially white crystalline solid upon drying.

Utilizing infrared spectrometer and chlorine analysis via Parr bomb, the solid is analyzed and shows that there is produced a compound having the following structural formula:

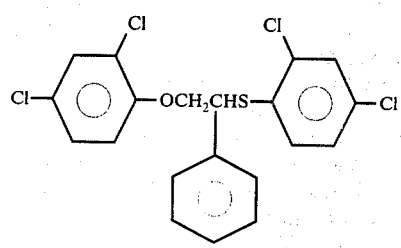

EXAMPLE XIII

Approximately 2000 ml of N,N-dimethylformamide, 189g (1.0 mole) of 4-bromothiophenol and 40g (1.0 mole) of sodium hydroxide pellets are charged to a 5000 ml reaction flask equipped with a mechanical stirrer, thermometer, reflux condenser, and stopped. The resultant mixture is heated to 130° C at which temperature there results a brown solution.

While maintaining this solution at about 130° C, there is added as rapidly as possible 520g (1.0 mole) of trans-1-(2,4,6-tribromophenoxy methyl)-4-bromomethyl)cyclohexane as a solid. The resulting mixture is maintained at about 130° C for approximately 120 minutes after the solid addition.

After this 120 minute period, the mixture is allowed to cool to room temperature (about 20° C - 25° C), diluted with 1000 ml of a 5% aqueous sodium hydroxide solution, and the resultant solid is recovered by filtration. The filter cake material is washed twice with 500 ml portions of water and finally with 500 ml of acetone. The material yields a substantially white crystalline solid upon drying.

Utilizing infrared spectrometer and bromine analysis via Parr bomb, the solid is analyzed and shows that there is produced a compound having the following structural formula:

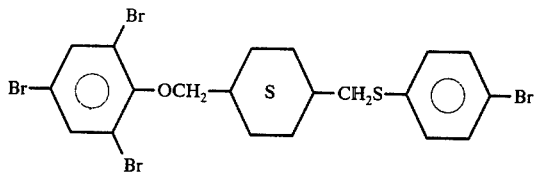

EXAMPLE XIV

An ABS plastic material, (Marbon TP-2098, a product of Marbon Division, Borg-Warner Corporation, Washington, West Virginia and containing antioxidants, lubricants, releasing agents and titanium dioxide pigment) is utilized as the base resin in order to prepare 26 formulations (plastic compositions). With the exception of formulation No. 1, the particular bis-phenoxy compound (and the antimony trioxide enhancing agent where indicated) is incorporated into the plastic by adding both to a Brabender mixer ("Plastic-Corder", Torque Rheometer, Model PLV-150, C. W. Brabender Instruments Inc., South Hackensack, N.J.). The mixer is equipped with a pair of roller type blades positioned within a head provided with heat transfer means.

The resultant mixture is heated to about 245° C.; at this temperature, it is in a molten state. The percentages by weight of each component utilized in the respective formulations are listed in Table II. Each formulation is discharged from the mixer and upon cooling solidifies and is ground into chips. The chips are subjected to compression molding in a Wabash press by placing said chips between two platens, the bottom of which contains four equal size depressions 3 inches by 5 inches by ⅛ inch deep. The top platen is then placed over the bottom platen and heat transfer means supplied thereto in order to melt said chips and thus provide solid samples (after cooling) for testing.

Portions of the solid samples of each respective formulation (Nos. 1-26) prepared according to the above described procedure are then subjected to two different standard flammability tests, i.e., UL 94 and ASTM D-2863-70. The UL 94 is, in general, the application of a burner to a test specimen (strip) for a certain period of time and observation of combustion, burning, and extinguishment. This procedure is fully set forth in Underwriters' Laboratories bulletin entitled UL 94, Standard for Safety, First Edition, September 1972 and which is incorporated herein by reference. ASTM No. D-2863-70 is a flammability test which correlates the flammability of a plastic specimen to the available oxygen in its immediate environment; this correlation is stated as an Oxygen Index, O.I., level predicated upon the percent oxygen in the gaseous medium which is required to just provide a steady state of continuous burning of the plastic specimen. This ASTM method is fully described in 1971 Annual Book of ASTM Standards — Part 27, published by the American Society For Testing and Materials, 1916 Race Street, Philadelphia, Pa.; this publication is to be considered as incorporated (in toto) herein by reference.

The results of these flammability tests are shown in Table II.

TABLE II

Flammability Data For ABS Plastic Compositions Containing Halogenated Aryl Compounds

| Formulation No. | Halogenated Aryl Compound No. | Enhancing Agent $Sb_2O_3$, % | Oxygen Index % | UL 94 |
|---|---|---|---|---|
| 1. | — | 0 | 0 | 18.5 | SB |
| 2. | 1 | 15 | 0 | 19.0 | SB |
| 3. | 1 | 15 | 5 | 23.0 | SB |
| 4. | 2 | 15 | 0 | 20.5 | SB |
| 5. | 2 | 15 | 5 | 32.0 | SE-0 |
| 6. | 3 | 15 | 0 | 21.0 | SB |
| 7. | 3 | 15 | 5 | 34.0 | SE-0 |
| 8. | 4 | 15 | 0 | 21.5 | SB |
| 9. | 4 | 15 | 5 | 33.0 | SE-0 |
| 10. | 32 | 15 | 0 | 23.5 | SB |
| 11. | 32 | 15 | 5 | 35.0 | SE-0 |
| 12. | 37 | 15 | 0 | 20.5 | SB |
| 13. | 37 | 15 | 5 | 28.5 | SB-1 |
| 14. | 65 | 15 | 0 | 21.0 | SB |
| 15. | 65 | 15 | 5 | 27.5 | SB-1 |
| 16. | 79 | 15 | 0 | 21.5 | SB |
| 17. | 79 | 15 | 5 | 28.0 | SB-1 |
| 18. | 122 | 15 | 0 | 21.0 | SB |
| 19. | 122 | 15 | 5 | 27.0 | SB-1 |
| 20. | 143 | 15 | 0 | 24.0 | SB |
| 21. | 143 | 15 | 5 | 36.5 | SE-0 |
| 22. | 159 | 15 | 0 | 21.0 | SB |
| 23. | 159 | 15 | 5 | 28.0 | SE-0 |
| 24. | 181 | 15 | 0 | 20.5 | SB |
| 25. | 181 | 15 | 5 | 27.0 | SB-1 |
| 26. | 205 | 15 | 5 | 34.0 | SB-0 |

Referring to Table II, the halogenated aryl compound number relates to the structural formulae heretofor set forth in Table I; a difference of 2% in the Oxygen Index values is considered significant; and the UL 94 values are on a graduated scale wherein the highest degree to lowest degree of the flame retardancy is respectively SE-0, SE-1, SE-2, SB and Burns.

The results shown in Table II demonstrate the unique effectiveness of these halogenated aryl compounds as flame retardants for ABS. Specifically, formulation No. 1 (the control) had a O.I. of 18.5 and UL 94 value of SB. In Nos. 2, 4, 6, 8, 10, 12, 14, 16, 18, 20, 22 and 24, the use of the particular halogenated aryl compound results in a significant increase (0.5-5.0%) in fire retardancy as measured by O.I. (While these formulations also had a SB rating, UL 94, the individual UL rating has a wide range of values and thus the O.I. number is, in this case, more indicative of increased flame retardancy).

The use of an enhancing agent such as $Sb_2O_3$ to promote a cooperative effect between such agent and the halogenated aryl compound is fully demonstrated via the results obtained from testing formulation Nos. 3, 5, 7, 9, 11, 13, 15, 17, 19, 21, 23, 25 and 26. The highest UL 94 ratings and significantly higher O.I. values (4.5-18.0% increase) are obtained.

EXAMPLE XV

Example XIV is repeated twice; once using a 10% halogenated aryl compound level and 3% $Sb_2O_3$ level and secondly, 20% and 10% levels respectively. At the 10%/3% level, the O.I. values and UL 94 ratings are slightly lower than the 15%/5% level of Example XIV. At the 20%/10% levels, the O.I. values and UL 94 ratings are slightly higher but basically the same as those obtained using 15%/5% level.

EXAMPLE XVI

Portions of the solid samples of Formulation Nos. 1-26 prepared according to the above described procedure of Example XIV are subjected to the following ASTM tests in order to ascertain other properties of the resultant plastic composition:

| (1) | Tensile Strength (at break) | ASTM Test No. D638-61T; |
| (2) | Flexural Strength | ASTM Test No. D790-63; |
| (3) | Flexural Modulus | ASTM Test No. D790-63; |
| (4) | Notched Izod Impact | ASTM Test No. D256-56; and |
| (5) | Heat Distortion Temperature (HDT) | ASTM Test No. D648-56. |

Each of the aforementioned ASTM Tests are standard tests in the art and are utilized collectively in order to ascertain the efficacy of a polymeric system as an overall flame retarded composition for commercial application. All of these ASTM Tests are to be considered as incorporated herein by reference.

The results of these ASTM tests show that the physical properties of the present invention compositions are basically the same (except O.I. and UL 94 values) as the plastic material without the flame retardant (i.e. formulation No. 1). Thus, there is no substantial adverse effect on the physical properties of the plastic material when the novel compounds are incorporated therein.

EXAMPLE XVII

The procedure of Examples XIV and XVI are repeated except that the enhancing agent used is zinc borate instead of $Sb_2O_3$. Substantially the same results are obtained using zinc borate as those obtained using $Sb_2O_3$.

EXAMPLE XVIII

Strip samples of each of Formulation Nos. 1 through 26 Table II, are subjected to light stability tests via the use of a "Weather-Ometer", model 25/18 W. R., Atlas Electrical Devices Company, Chicago, Illinois. Utilizing an operating temperature of 145° F and a 50% relative humidity, each strip is subjected to 200 hours of "simulated daylight" via the use of a carbon arc. The results show that after 200 hours, there is no significant discoloration in any strip tested and which demonstrates that the present invention compositions are highly resistant to deterioration by light.

EXAMPLE XIX

Samples of each of Formulation Nos. 1 through 26 Table II, are subjected to temperature (thermal) stability tests via the use of thermal gravimetric analysis (TGA). This test employed the use of a "Thermal Balance", model TGS-1, Perkin-Elmer Corporation, Norwalk, Connecticut and an electrical balance, Cahn 2580 model, Cahn Instrument Company, Paramount, California. The results of these tests show that the halogenated aryl compound containing Formulations had more than adequate stability for melt processing and subsequent heat aging (i.e., high temperature applications) and thus demonstrating that the particular halogenated aryl are quite compatible with the plastic material. The halogenated aryl compound stability thus aids in providing sufficient flame retardancy at the plastic decomposition temperature. This test also demonstrates that these compounds do not exhibit migration.

In view of the foregoing Examples and remarks, it is seen that the plastic compositions, which incorporate these compounds, possess characteristics which have been unobtainable in the prior art. Thus, the use of these compounds in the above described plastic material as flame retardants therefor is quite unique since it is not possible to predict the effectiveness and functionality of any particular material in any polymer system until it is actively undergone incorporation therein and the resultant plastic composition tested according to various ASTM Standards. Furthermore, it is necessary, in order to have commercial utility, that the resultant flame retarded plastic composition possess characteristics such as being non-toxic. Use of these compounds in the plastic material has accomplished all of these objectives.

The above examples have been described in the foregoing specification for the purpose of illustration and not limitation. Many other modifications and ramifications will naturally suggest themselves to those skilled in the art based on this disclosure. These are intended to be comprehended as within the scope of this invention.

What is claimed is:

1. A halogenated aryl compound having the formula

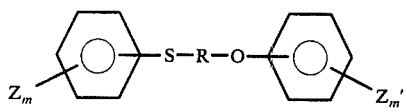

wherein R is an alkylene group having from 1 to 6 carbon atoms, Z is selected from the group consisting of bromine or chlorine, and $m$ and $m'$ are integers having a value of 1–5.

2. A halogenated aryl compound having the formula

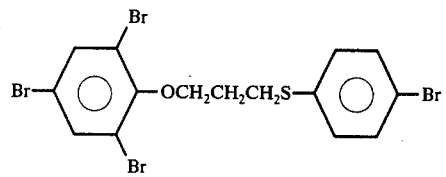

* * * * *